United States Patent [19]
Ghosez et al.

[11] 3,947,469
[45] Mar. 30, 1976

[54] 3-(1,3-DITHIAN-2-YL)-4-CYCLO-PENTENE-2-CARBOXYLIC ACIDS, ESTERS AND AMIDES

[75] Inventors: Leon Ghosez, Heverlee; Eric Cossement, Brussels; Robert Biname, Kraainem, all of Belgium

[73] Assignee: Recherche et Industrie Therapeutiques (R.I.T.), Belgium

[22] Filed: Sept. 9, 1974

[21] Appl. No.: 504,394

[30] Foreign Application Priority Data
Sept. 17, 1973 Luxemburg............................ 68427

[52] U.S. Cl...... 260/327 M; 260/468 D; 260/468 J; 260/468 L; 260/470; 260/514 D; 260/514 J; 260/514 L; 260/516; 260/544 Y; 260/557 R; 260/558 S; 260/586 R; 260/586 F; 260/593 R; 260/598; 260/590 C; 260/590 D; 260/585.5
[51] Int. Cl.$^2$........................................ C07D 339/08
[58] Field of Search............ 260/327 M, 514 J, 516, 260/468 J, 470, 557 R, 558 S

[56] References Cited
OTHER PUBLICATIONS
Ghosez et al., Tetrahedron Letters, 1966, pp. 135–139.

J. Chem. Soc. (C), 1971, pp. 1764–1769, Brook et al.

J. Org. Chem. 28 : 1433–1435, (1963), McDonald et al.

*Primary Examiner*—Sherman D. Winters
*Attorney, Agent, or Firm*—Alan D. Lourie; William H. Edgerton

[57] ABSTRACT

The invention relates to the stereoisomers of novel cyclopentene derivatives and to the preparation thereof.

The cyclopentene derivatives are obtained by cycloaddition reaction between cyclopentadiene and a mono-or bis-thioalkyl (or aryl) ketene and reaction between the obtained product and a nucleophile agent.

The compounds of the invention are intermediate products valuable for the preparation of different compounds, among which compounds of the prostaglandin type.

8 Claims, No Drawings

3-(1,3-DITHIAN-2-YL)-4-CYCLO-PENTENE-2-CARBOXYLIC ACIDS, ESTERS AND AMIDES

The present invention relates to stereoisomers of cyclopentene derivatives represented by the structural formula I

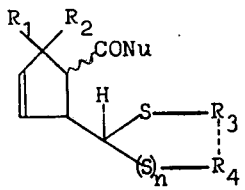

formula I wherein $R_1$ and $R_2$ represent hydrogen,

Nu is a nucleophile residue, more particularly hydroxy, lower alkoxy (containing from one to four carbon atoms), mono- or di-lower alkyl (containing from one to four carbon atoms) amino n is 0 or 1

$R_3$ and $R_4$ are identical or different, and each of them represents a lower alkyl radical (containing from one to four carbon atoms) or an aryl radical and, when $n = 1$, $R_3$ and $R_4$ taken together may also represent a lower alkylene group (containing from two or three carbon atoms)

and the preparation thereof, as well as the new compounds represented by the structural formulae II and III hereafter described for the preparation of the derivatives of formula I and the preparation of the compounds of formulae II and III. According to the invention, the stereoisomers of cyclopentene derivatives of formula I are prepared by a cycloaddition reaction between an unsubstituted cyclopentadiene and a ketene derivative belonging to the group comprising the mono- and bis-thioalkyl (aryl) ketenes (each alkyl containing from one to four carbon atoms), the 2-carbonyl-1,3-dithiolane and the 2-carbonyl-1.3-dithiane represented by the general formula II

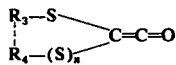

formula II wherein $R_3$, $R_4$ and n are as defined in the formula I, to yield the corresponding spirocyclobutanone represented by the structural formula III

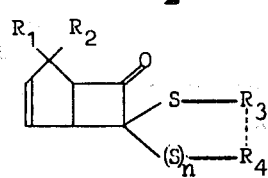

formula III wherein $R_1$, $R_2$, $R_3$, $R_4$ and n are as defined in the formula I, said corresponding spirocyclobutanone being easily transformed into cyclopentene derivative of formula I by reaction with a nucleophile agent.

The compounds of formulae I, II and III are valuable products for the pharmaceutical industry as intermediates for the preparation of prostaglandins and prostaglandins like compounds. The compounds of formula I are also valuable intermediates for the cosmetic industry and the compounds of formula III are valuable products for the phytopharmaceutical industry, for example, in the preparation of pesticides. The compounds of formula II are new reagents for the cycloaddition reaction.

The cycloaddition to unsubstituted cyclopentadiene is already known to the art, for example, by U.S. Pat. No. 3,549,769 but, prior to this invention, the herein described ketene derivatives were not known as reagents for cycloaddition. The compounds of formula I obtained from said reagents provide more advantageous possibilities of reactivity in position 3 than those which are provided by the corresponding gem-dichloro derivatives obtained from the dihaloketene derivatives previously described for the cycloaddition reaction.

The thioacetal group indeed prevents competitive reactions encountered with gem-dihalo derivatives and, moreover, due to its easier hydrolysis, it provides better precursor for lateral chains.

For example, as indicated in the following scheme A, the CONu group present in the compounds of the formula I may be first transformed into $CH_2OH$ group by reduction with lithium aluminium hydride and the thioacetal group may be transformed into aldehyde group by hydrolysis with an aqueous solution of mercuric chloride (E.J. Corey et al., J. Org. Chem. 36, 3553, 1971). The obtained product is then condensed with the sodioderivative of dimethyl 2-oxo heptylphosphonate and the $CH_2OH$ group is oxidized, for example, with Jones reagent to aldehyde group which may undergo a Wittig reaction with (5-carboxypentyl) triphenyl phosphonium bromide (E.J. Corey et al., J. Amer. Chem. Soc. 92. 397, 1970).

The ketone group is then reduced to hydroxy group, for example, with zinc borohydride. By catalytic hydrogenation, the corresponding deoxyprostaglandin is obtained.

SCHEME A

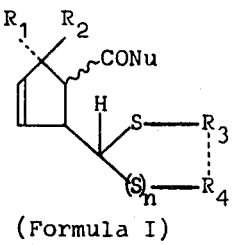

(Formula I)

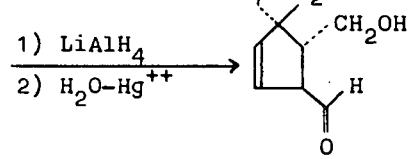

1) $LiAlH_4$
2) $H_2O-Hg^{++}$

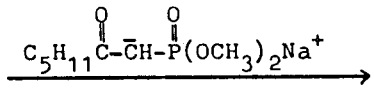

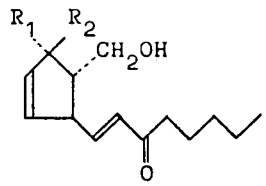

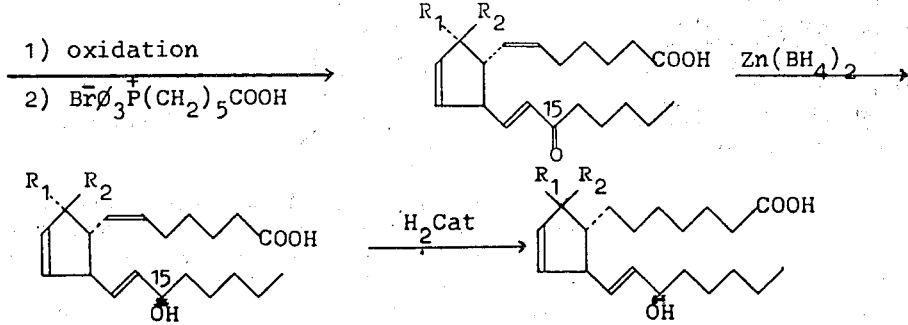

The following scheme B describes the preparation of compounds of formula I, according to the invention.

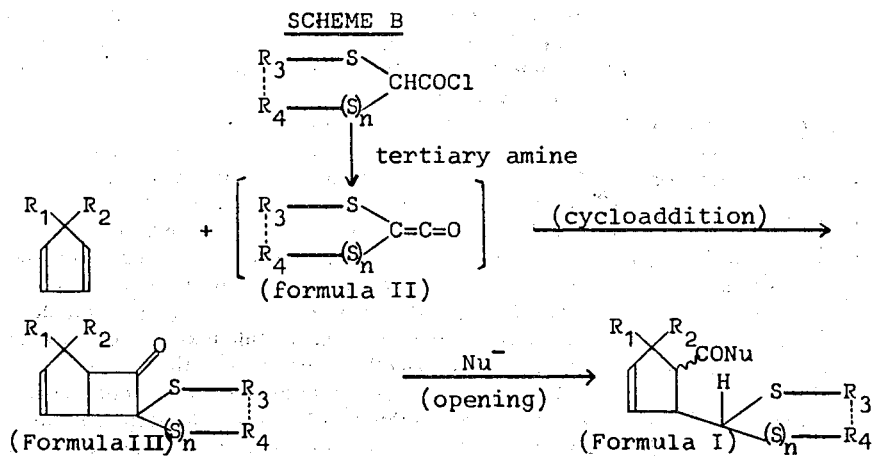

In scheme B, $R_1$, $R_2$, $R_3$, $R_4$, Nu and $n$ are as defined in formula I and $Nu^-$ represents a nucleophile reagent.

The process, according to the invention, consists in treating in a non reactive solvent, e.g. ether, cyclopentadiene with a ketene derivative of formula II obtained in situ by reaction between a tertiary amine and the corresponding acid chloride and treating the so-obtained cycloaddition compound with a nucleophile reagent.

Among the nucleophile agents are, for example, alkali metal hydroxides, alcoholates, and amides and primary aliphatic amines (containing from one to four carbon atoms). According to the used nucleophile reagent, the obtained products of formula I are provided with cis or trans configuration. They are autoconvertible, for example, following the hereunder scheme C.

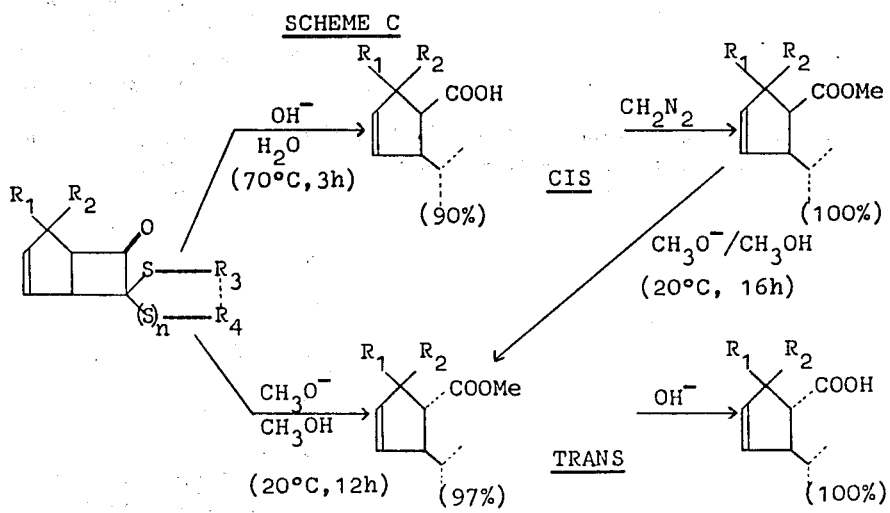

In scheme C, $R_1$, $R_2$, $R_3$, $R_4$ and n are as hereabove defined.

In the following examples which are presented to illustrate the invention further but are not be construed to limit the scope thereof, the indicated infra-red spectra have been determined by a PERKIN-ELMER 257 spectrometer and calibrated by comparison with the spectrum of polystyrene; the nuclear magnetic resonance spectra (NMR) have been recorded on a VARIAN T 60 spectrograph(60 MHz) at room temperature, using tetramethylsilane as internal reference; the values being expressed in δ and the nmr spectra have been recorded on a VARIAN HA100 or XL100 (100 MHz) at room temperature, using tetramethylsilane as internal reference.

EXAMPLE 1

1,3-Dithiane-2-carboxylic acid.

In a one liter three-necked reaction flask equipped with a water-separator device (Dean-Stark) and a reflux condenser there are added 700 ml. of benzene, 54 g (0.5 mol) of 1,3-propanedithiol 46 g (0.5 mol) of monohydrated glyoxylic acid and 0.5 g (2.9 mmol) toluene-p-sulfonic acid. The mixture is heated to reflux with stirring. After 18 ml. (1 mol) water has been condensed, the hot solution is decanted from the precipitate formed on the container walls. The solvent is evaporated under reduced pressure and the residue is crystallized from toluene to yield 1,3-dithiane-2-carboxylic acid.

Melting point : 114.1° C.
NMR spectrum : (CDCl₃)

| H | δ | Mult. | Int. |
|---|---|---|---|
| Ha-b | 2 to 3.7 | m | 6 |
| Hc | 4.22 | s | 1 |
| Hd | 11.5 | s | 1 |

EXAMPLE 2

1.3-Dithiane-2-carboxylic acid chloride.

In a 500 ml. reaction flask equipped with a reflux condenser connected with a wash-bottle containing $H_2SO_4$, there are added 250 ml. of anhydrous benzene (distilled upon sodium), 42 g (0.25 mol) of 1.3-dithiane-2-carboxylic acid (as prepared in example 1) and 28 ml. (0.4 mol) of freshly distilled oxalyl chloride. The mixture is stirred at room temperature and at the end of gaseous evolution, the mixture is heated up to 45° C to complete the gas evolution. The solvent and the excess of oxalyl chloride are evaporated under reduced pressure and the residue is crystallized from dried cyclohexane to yield 1,3-dithiane-2-carboxylic acid chloride.

Melting point : 51.4° C.
NMR spectrum :

| H | δ | Mult. | Int. |
|---|---|---|---|
| Ha-b | 1.7–3.7 | m | 6 |
| Hc | 4.37 | s | 1 |

EXAMPLE 3

Spiro[(bicyclo[3.2.0]hept-2-en-6-one)-7.2'-(1',3'-dithiane)].

In a one liter three-necked reaction flask equipped with a reflux condenser, a cock-funnel and a mechanical stirrer, there are added 12 g (0.2 mol) of freshly distilled cyclopentadiene, 10.1 g (0.1 mol) of dried triethylamine and 200 ml. of anhydrous ether. To the solution heated to 35° C are added dropwise and within one hour 18g(0.1 mol) of 1.3-dithiane-2-carboxylic acid chloride (as prepared in example 2). The mixture is stirred at 35°C for 1 hour and then for 12 hours at room temperature. Triethylamine chlorhydrate is filtered therefrom and washed with ether. The filtrate is treated with an aqueous solution of 10% HCl and then with an aqueous solution of 10% sodium carbonate. The organic phase is separated, dried over anhydrous sodium sulfate, filtered and the solvent is evaporated under reduced pressure. The residue is sublimated at about 50° C under $10^{-2}$mm Hg and purified by crystallization from methanol to yield spiro[(bicyclo[3.2.0] hept2-en-6-one)-7.2'-(1',3'-dithiane)].

Melting point : 71.9° C.
IR spectrum(KBr)2910,1774, 1605, 1429, 1421, 1412 cm⁻¹.
NMR spectrum (CDCl₃) :

| H | δ | Mult. | Int. |
|---|---|---|---|
| Ha | 2.02 | m | 2 |
| Hb+Hb' | 2.75 | m | 3 |
| Hc | 3.3 | m | 4 |
| Hd | 4.37 | ddd | 1 |
| He | 5.93 | m | 2 |

EXAMPLE 4

Cis-3-(1,3-dithian-2-yl)-4-cyclopentene-2-carboxylic acid.

In a 50 ml. reaction flask equipped with a reflux condenser there are added 1.06 g (5 mmol) of spiro[(-bicyclo[3.2.0]hept-2-en-6-one)-7.2-(1',3'dithiane)] (as prepared in example 3), 200 mg (5 mmol) of sodium hydroxide and 30 ml. of distilled water. The mixture is heated for 3 hours at 70° C with stirring, cooled, acidified with 10% HCl and extracted with ether. The ethereal layer is dried over anhydrous sodium sulfate, filtered and evaporated under reduced pressure. The residue is crystallized from a mixture of cyclohexane : carbon tetrachloride (9:1) to yield cis-3-(1.3-dithian2-yl)-4-cyclopentene-2-carboxylic acid.

Melting point : 106.5°–106.6° C.
IR spectrum : (KBr) : 3045, 2900, 1701, 1605, 1422, 1412 cm⁻¹.
NMR spectrum : (CDCl₃)

| H | δ |
|---|---|
| 2 Ha | 2.0 |
| 4Hb+2Hc | 2.83 |
| 2 Hd | 3.4 |
| He | 4.65 |
| 2 Hf | 5.93 |
| Hg | 11.4 |

EXAMPLE 5

Cis-methyl-3-(1,3-dithian-2yl)-4-cyclopentene-2-carboxylate.

214 mg (0.93 mmole) of cis-3-(1,3-dithian-2-yl)-4-cyclopentene-2-carboxylic acid (as prepared in example 4) are dissolved in 3 ml. of dried methanol. To the cooled mixture (0° C), there is added an ethereal solution of diazomethane up to persistente yellow colour. The solution is stirred for 3 hours at room temperature, the solvent is evaporated under reduced pressure and the oily residue is purified by column chromatography (eluant $C_6H_6/CH_3CO_2C_2H_5$ : 80/20) to yield cis-methyl-3-(1,3-dithian-2-yl)-4-cyclopentene-2-carboxylate.

IR spectrum : (film) : 2910, 1730, 1617, 1430 cm$^{-1}$.
NMR spectrum : (CDCl$_3$) : H$_7$ = 4.55 δ

EXAMPLE 6

Trans-methyl-3-(1.3-dithian-2-yl)-4-cyclopentene-2-carboxylate.

In a 50 ml. reaction flask equipped with a reflux condenser there are added 1.06 g (5 mmol) of spiro [(bicyclo[3.2.0]hept-2-en-6-one)-7.2-(1′,3′-dithiane)] (as prepared in example 3) and 270 mg (5 mmol) of sodium methylate dissolved in 30 ml. of dried methanol. The mixture is stirred for 15 hours at room temperature and the methanol is evaporated under reduced pressure. The residue is taken up in 25 ml. of distilled water and the solution is extracted with 50 ml. of ether. The ethereal layer is dried over anhydrous sodium sulfate and filtered. The filtrate is evaporated under reduced pressure and the oily residue is purified by column chromatography (eluant : $C_6H_6/CH_3COOC_2H_5$ : 80/20) to yield trans-methyl-3-(1.3-dithian2-yl)-4-cyclopentene-2-carboxylate.

IR spectrum : (film) : 1735, 1602, 1442 cm$^{-1}$.
NMR spectrum : (CDCl$_3$) : H$_7$ = 4.2 δ

EXAMPLE 7

Trans-3-(1.3-dithian-2-yl)-4-cyclopentene-2-carboxylic acid.

In a 10 ml. reaction flask equipped with a reflux condenser, there are added 226 mg (0.93 mmol) of trans-methyl-3-(1.3-dithian-2-yl)-4-cyclopentene-2-carboxylate (as prepared in example 6) dissolved in 5 ml. of distilled water and a few mg of sodium hydroxide dissolved in one ml. of distilled water. The mixture is heated to 80° C for 3 hours, then cooled and neutralized by 5% HCl. The solution is extracted with ether and the ethereal layer is dried over anhydrous sodium sulfate, filtered and evaporated under reduced pressure to yield trans-3-(1,3-dithian-2-yl)-4-cyclopentene-2-carboxylic acid.

Melting point : 112.9° C.
NMR spectrum : (CDCl$_3$) :

| H | δ | Mult. | Int. |
|---|---|---|---|
| Ha | 2.1 | m | 2 |
| Hb+Hc | 2.9 | m | 6 |
| Hd+He | 3.4 | m | 2 |
| Hf | 4.2 | d | 1 |
| Hg | 5.8 | ~s | 2 |

EXAMPLE 8

Trans-2-methyl-3-(1.3-dithian-2-yl)-4-cyclopentenecarboxylate.

To cis-methyl-3-(1.3-dithian-2-yl)-4-cyclopentene-2-carboxylate dissolved in deuterated methanol there are added two or three drops of sodium methylate dissolved in deuterated methanol. The reaction is followed by NMR method. After a 16 hour reaction, the whole cis isomer is transformed into the corresponding trans isomer. Deuterated methanol is evaporated, the obtained residue is dissolved in 1 ml. of ether and quickly washed with a 3% HCl solution. The organic layer is dried over MgSO$_4$, filtered and the filtrate is evaporated to yield a product with the same characteristics as those of the trans derivative prepared in example 6.

EXAMPLE 9

3-(1.3-Dithian-2-yl)-4-cyclopentene-N,N-dimethyl-2-carboxamide.

In a 50 ml. three-necked reaction flask and to 20 ml. of dimethylamine condensed at a temperature inferior to 40° C, there is added with a syringue 4 ml. of butyllithium dissolved in hexane (1.62 N). The temperature of the medium is allowed to rise −20° C. In the meantime, in 5 ml. of dimethylamine condensed in a cooling cock-funnel (CO$_2$-iC$_3$H$_7$OH), there is dissolved 1.1 g (5 mmol) of spiro[(bicyclo[3.2.0]hept-2-en-6-one)-7.2′-(1′,3′-dithiane)](as prepared in example 3). This mixture is added dropwise to the amide as prepared hereinabove in the reaction flask. The medium is allowed to react at −10° C for 2 hours, 20 ml. of ether is added and the solution is allowed to react at room temperature for 12 hours. Water (20 ml.) is then added and the solution is extracted with 3 × 15 ml. of ether. The ethereal layer is dried over CaSO$_4$, filtered, evaporated under reduced pressure and the residue is crystallized from a mixture of carbon tetrachloride and cyclohexane to yield 3-(1.3-dithian-2-yl)-4-cyclopentene-N,N-dimethyl-2-carboxamide.

Melting point: 87.3° C.
NMR spectrum: (CDCl$_3$):

| H | δ | Mult. | Int. |
|---|---|---|---|
| Ha | 2.15 | m | 2 |
| Hb+Hc<br>Hd+He | 2.2–3 | m | 14 |
| Hf | 4.35 | d | 1 |
| Hg | 5.9 | m | 2 |

EXAMPLE 10

3-(1.3-Dithian-2-yl)-4-cyclopentene-N-butyl-2-carboxamide.

In a 50 ml. reaction flask equipped with a reflux condenser there are added 1.06 g (5 mmol) of spiro[(-bicyclo [3.2.0]helt-2-en-6-one)-7.2′-(1′,3′-dithiane)]-

(as prepared in example 3), 0.73 g (10 mmol) of n-butylamine and 30 ml. of anhydrous benzene. The mixture is refluxed with stirring for 14 hours. The solvent and the unreacted amine are removed by evaporation and the residue is crystallized from a mixture of pentane and carbon tetrachloride (8/2) to yield 3-(1.3-dithian-2-yl)-4-cyclopentene-N-butyl-2-carboxamide.

NMR spectrum: (CDCl$_3$):

| H | δ | Mult. | Int. |
|---|---|---|---|
| Ha | 1.53–1.74 | 2 s | 6 |
| Hb | 2.07 | m | 2 |
| Hc | 2.5 | s | 6 |
| Hd | 2.6 – 3.6 | m | 4 |
| He | 4.3 | s | 1 |

EXAMPLE 11

1.3-Dithiolane-2-carboxylic acid.

In a 500 ml. reaction flask equipped with a reflux condenser, there are added 16.5 g (0.175 mol) of 1.2-ethanedithiol, 16 g (0.173 mol) of monohydrated glyoxylic acid, 250 ml. of benzene and 25 ml. of ethylfluoboroetherate. The mixture is stirred under reflux for 4 hours and then cooled. Distilled water (100 ml.) is added thereto, the solution is decanted and the aqueous phase is extracted with ether. The ethereal layers are dried over anhydrous sodium sulfate, filtered and evaporated under reduced pressure and the residue is crystallized from toluene to yield 1.3-dithiolane-2-carboxylic acid.

Melting point: 107°–8° C.
IR spectrum: (KBr): 3050, 2915, 1710, 1410 cm$^{-1}$.
NMR spectrum : (CDCl$_3$):

| H | δ | Mult. | Int. |
|---|---|---|---|
| Ha | 3.43 | m | 4 |
| Hb | 4.88 | s | 1 |
| Hc | 11.68 | s | 1 |

EXAMPLE 12

1.3-dithiolane-2-carboxylic acid chloride.

In a 500 ml. reaction flask equipped with a reflux condenser connected with a wash-bottle containing H$_2$SO$_4$, there are added 21.8 g (0.145 mol) of 1.3-dithiolane-2-carboxylic acid (as prepared in example 11), 300 ml. of anhydrous benzene (distilled on sodium) and 35.7 g (0.3 mole) of freshly distilled thionyl chloride. The mixture is stirred at room temperature for 12 hours and then for 2 hours at 45°–50° C maximum. The solvent and the excess of thionyl chloride are removed by evaporation under reduced pressure and the residue is distilled at 80°–85° C under 0.05 mm Hg to yield 1.3-dithiolane-2-carboxylic acid chloride.

IR spectrum: (CHCl$_3$): 2930, 1787, 1760, 1420.
NMR spectrum: (CDCl$_3$)

| H | δ | Mult. | Int. |
|---|---|---|---|
| Ha | 3.43 | s | 4 |
| Hb | 5.19 | s | 1 |

EXAMPLE 13

Spiro[(bicyclo[3.2.0]hept-2-en-6-one)-7.2'-(1',3'-dithiolane)].

In a 500 ml. three-necked reaction flask equipped with a reflux condenser connected with a calcium chloride tube, a cock funnel with pressure compensation and a mechanical stirrer, there are added 200 ml. of anhydrous ether, 7.1 g (0.07 mol) of dried triethylamine and 13.9 g (0.21 mol) of freshly distilled cyclopentadiene. To the mixture heated to reflux are dropped 11.83 g (0.07 mol) of 1.3-dithiolane-2-carboxylic acid chloride (as prepared in example 12) dissolved in 50 ml. of anhydrous ether. The medium is vigorously stirred at reflux temperature for 2 hours and then for 12 hours at room temperature. Triethylamine chlorhydrate is filtered therefrom and washed with ether. The filtrate is treated with an aqueous solution of 5 % HCl and then with an aqueous solution of 5 % sodium carbonate. The ethereal layer is separated, dried over anhydrous sodium sulfate, filtered and the solvent is eliminated by evaporation. The residue is purified by chromatography on Silicagel (eluant: CHCl$_3$) and then distilled under reduced pressure (110° C/10$^{-2}$ mm). The condensate is further purified by sublimation to yield spiro[(bicyclo[3.2.0]hept-2-en-6-one)-7.2'-/1'-3'-dithiolane)].

Melting point: 49.5° C.
IR spectrum: (KBr): 2925, 2830, 1780, 1602, 1438, 1418 cm$^{-1}$.
NMR spectrum: (CDCl$_3$) :

| H | δ | Mult. | Int. |
|---|---|---|---|
| Ha | 2.66 | m | 2 |
| Hb | 3.3 | s | 4 |
| Hc | 3.7 | m | 1 |
| Hd | 4.06 | ddd | 1 |
| He | 6.0 | m | 2 |

EXAMPLE 14

Cis-3-(1.3-dithiolan-2-yl)-4-cyclopentene-2-carboxylic acid.

Using the procedure described in example 4 but replacing spiro[(bicyclo[3.2.0]hept-2-en-6-one)-7.2'-(1',3'-dithiane)] by 5 mmol of spiro[(bicyclo[3.2.0-]hept-2-en-6-one)-7.2'-(1',3'-dithiolane)] (as prepared in example 13), cis-3-(1.3-dithiolan-2-yl)-4-cyclopentene-2-carboxylic acid is obtained.

EXAMPLE 15

Cis-methyl-3-(1,3-dithiolan-2-yl)-4-cyclopentene-2-carboxylate.

Using the procedure described in example 5 but replacing cis-3-(1.3-dithian-2-yl)-4-cyclopentene-2-carboxylic acid by 0.93 mmol of cis-3-(1.3-dithiolan-2-yl)-4-cyclopentene-2-carboxylic acid (as prepared in example 14), cis-methyl-3-(1.3-dithiolan-2-yl)-4-cyclo-pentene-2-carboxylate is obtained.

EXAMPLE 16

Trans-methyl-3-(1.3-dithiolan-2-yl)-4-cyclopentene-2-carboxylate.

Using the procedure described in example 6 but replacing spiro[(bicyclo[3.2.0]hept-2-en-6-one)-7.2'-(1',3'-dithiane)] by 5 mmol of spiro[(bicyclo[3.2.0-

]hept-2-en-6-one)-7.2'-(1',3'-dithiolane)] (as prepared in example 13), trans-methyl-3-(1.3-dithiolan-2-yl)-4-cyclopentene-2-carboxylate is obtained.

EXAMPLE 17

Trans-3-(1.3-dithiolan-2-yl)-4-cyclopentene-2-carboxylic acid.

Using the procedure described in example 7 but replacing trans-methyl-3-(1.3-dithian-2-yl)-4-cyclopentene-2-carboxylate by 0.93 mmol of trans-2-methyl-3-(1.3-dithiolan-2-yl)-4-cyclopentenecarboxylate (as prepared in example 16), trans-3-(1.3-dithiolan-2-yl)-4-cyclopentene-2-carboxylic acid is obtained.

EXAMPLE 18

Trans-methyl-3-(1.3-dithiolan-2-yl)-4-cyclopentene-2-carboxylate.

Using the procedure described in example 8 but replacing cis-methyl-3-(1.3-dithian-2-yl)-4-cyclo-pentene-2-carboxylate by cis-methyl-3-(1.3-dithiolan-2-yl)-4-cyclopentene-2-carboxylate (as prepared in example 15), trans-methyl-3-(1.3-dithiolan-2-yl)-4-cyclopentene-2-carboxylate is obtained.

EXAMPLE 19

3-(1.3-dithiolan-2-yl)-4-cyclopentene-N,N-dimethyl-2-carboxamide.

Using the procedure described in example 9 but replacing spiro[(bicyclo[3.2.0]hept-2-en-6-one)-7.2'-(1',3'-dithiane)] by 5 mmol of spiro[(bicyclo[3.2.0]hept-2-en-6-one)-7.2'-(1',3'-dithiolane)] (as prepared in example 13), 3-(1.3-dithiolan-2-yl)-4-cyclopentene-N,N-dimethyl-2-carboxamide is obtained.

EXAMPLE 20

3-(1.3-dithiolan-2-yl)-4-cyclopentene-N-butyl-2-carboxamide.

Using the procedure described in example 10 but replacing spiro[(bicyclo[3.2.0]hept-2-en-6-one)-7.2'-(1',3'-dithiane)] by 5 mmol of spiro[(bicyclo[3.2.0]hept-2-en-6-one)-7.2'-(1',3'-dithiolane)] (as prepared in example 13), 3-(1.3-dithiolan-2-yl)-4-cyclopentene-N-butyl-2-carboxamide is obtained.

EXAMPLE 21

2-Phenylthiopropionic acid.

In a one liter conical flask topped by a cockfunnel with pressure compensation and equipped with a magnetic stirrer there are added with stirring 71.8 g (654 mmol) of thiophenol and a solution of 57 g (1420 mmol) of sodium hydroxide in 115 ml. of distilled water. To this mixture there is added slowly 100 g (654 mmol) of 2-bromopropionic acid neutralized by a solution of 73 g (820 mmol) sodium acetate in 140 ml. of distilled water. After a 45 minute reaction, the solution is brought to pH 5 with 30 % HCl, chloroform (200 ml.) is added thereto and the solution is decanted. After a second extraction, the combined organic phases are washed with 5 % HCl and decanted. The organic layer is dried over calcium chloride, filtered and eliminated by evaporation. The oily residue is purified by distillation under reduced pressure (137° C/0.7 mm) to yield 2-phenylthiopropionic acid.

EXAMPLE 22

2-Phenylthiopropionic acid chloride.

In a 500 ml. three-necked reaction flask containing 45 g (247 mmol) of 2-phenylthiopropionic acid (as prepared in example 21) in 280 ml. of anhydrous benzene equipped with a magnetic stirrer, a reflux condenser connected with a wash-bottle containing $H_2SO_4$ there are added carefully by a cock-funnel with pressure compensation, 32 g (270 mmol) of thionyl chloride. The mixture is gradually heated until reflux with vigorous stirring. When gas evolution is completed, the solvent is evaporated and the residue is purified by distillation under reduced pressure (106° C/4 mm) to yield 2-phenylthiopropionic acid chloride.

EXAMPLE 23

7-Methyl-7-phenylthio bicyclo[3.2.0]hept-2-en-6-one.

In a 500 ml. three-necked reaction flask equipped with a mechanical stirrer, a reflux condenser adapted with a Silicagel tube and a 100 ml. cock-funnel with pressure compensation there are added 160 ml. of anhydrous ether, 6.85 g (60 mmol) of triethylamine and 13 g (147 mmol) of freshly distilled cyclopentadiene. To the refluxed and vigorously stirred mixture there is added dropwise 13.56g(74.5 mmol) of 2-phenylthiopropionic acid chloride (as prepared in example 22) in 90 ml. of anhydrous ether. The reaction medium is refluxed for two hours with stirring and maintained at room temperature for 3 hours. Triethylamine hydrochloride is filtered therefrom and the filtrate is eliminated by evaporation. The oily-brown residue is purified by sublimation under reduced pressure (40°–50° C/0.1 to 0.5 mm) to yield 7-methyl-7-phenylthio-bicyclo[3.2.0]hept-2-en-6-one.

Melting point: 49° C.
Analysis:

|   | Calculated | found |
|---|---|---|
| C | 73.007 | 73.02 |
| H | 6.127 | 6.26 |
| O | 6.946 | 7.06 |

EXAMPLE 24

3-(1-phenylthioethyl)-4-cyclopentene-N-ethyl-2-carboxamide.

In a 100 ml. three-necked reaction flask and to 20 ml. of diethylamine condensed at a temperature inferior to 40° C there are added under dry nitrogen atmosphere 45.7 mg of finely divided lithium and a trace of ferric nitrate. The temperature of the medium is allowed to reach $-20°$ C. In the meantime, in 20 ml. of dimethylamine condensed in a cooling cock-funnel ($CO_2$-acetone), there is dissolved 5 g (6.52 mmol) of 7-methyl-7-phenylthiobicyclo[3.2.0]hept-2-2-en-6-one (as prepared in example 23). This mixture is dropped into the amide formed hereinabove in the reaction flask. The reaction medium is allowed to react at $-10°$ C for 2 hours and one of ammonium chloride is added thereto. The solvent is allowed to evaporate and the residue is taken up in 100 ml. of chloroform. The solution is washed several times with distilled water and the organic layer is decanted, dried over anhydrous sodium sulfate, filtered and evaporated under reduced pressure. The residue is crystallized from a mixture of ether and petroleum ether to yield 3-(1-phenylthioethyl)-4-cyclopentene-N-ethyl-2-carboxamide.

Melting point: 92°–93° C.

Analysis:

|   | calculated | found |
|---|---|---|
| C | 69.78 | 69.90 |
| H | 7.69 | 7.59 |
| O | 5.81 | 5.87 |

EXAMPLE 25

3-(1-Phenylthioethyl)-4-cyclopentene-2-carboxamide.

The procedure described in example 24 is repeated while replacing ethylamine for liquid ammonia. After standing for 7 hours, the mixture is neutralized by one-gof ammonium chloride and ammonia is evaporated. The residue is taken up in ether and the solution is salted out with brine. The organic layer is dried over anhydrous sodium sulfate, filtered and the filtrate is evaporated under reduced pressure. The residue is crystallized from ether to yield 3-(1-phenylthioethyl)-4-cyclopentene-2-carboxamide.

Melting point: 109° C.

Analysis:

|   | calculated | found |
|---|---|---|
| C | 67.98 | 67.86 |
| H | 6.93 | 6.73 |
| N | 5.66 | 5.64 |
| S | 12.96 | 12.82 |

We claim:

1. A compound of the formula

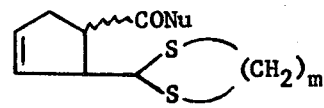

where Nu is hydroxy, lower alkoxy of 1 to 4 carbon atoms, amino, lower alkylamino of 1 to 4 carbon atoms, or dilower alkylamino, each alkyl having 1 to 4 carbon atoms;

$m$ is 2 or 3; and the wavy line indicates an $\alpha$ or $\beta$-configuration.

2. A compound according to claim 1 being cis-3-(1,3-dithian-2-yl)-4-cyclopentene-2-carboxylic acid.

3. A compound according to claim 1 being cis-methyl 3-(1,3-dithian-2-yl)-4-cyclopentene-2-carboxylate.

4. A compound according to claim 1 being trans-methyl 3-(1,3-dithian-2-yl)-4-cyclopentene-2-carboxylate.

5. A compound according to claim 1 being trans-3-(1,3-dithian-2-yl)-4-cyclopentene-2-carboxylic acid.

6. A compound according to claim 1 being 3-(1,3-dithian-2-yl)-4-cyclopentene-N,N-dimethyl-2-carboxamide.

7. A compound according to claim 1 being 3-(1,3-dithian-2-yl)-4-cyclopentene-N-butyl-2-carboxamide.

8. A compound according to claim 1, in which m is 2 and Nu is hydroxy or lower alkoxy of 1 to 4 carbon atoms.

* * * * *

UNITED STATES PATENT AND TRADEMARK OFFICE
CERTIFICATE OF CORRECTION

PATENT NO. : 3,947,469
DATED : March 30, 1976
INVENTOR(S) : Leon Ghosez, Eric Cossement, and Robert Biname It is certified that error appears in the above-identified patent and that said Letters Patent are hereby corrected as shown below:

Column 6, line 30, change ---hept2-en-6-one)--- to "hept-2-en-6-one"

Column 6, line 32, underline "1774"

Column 6, line 60, change ---(1.3-dithian2- --- to "(1.3-dithian-2-"

Column 6, line 63, underline "1701"

Column 7, line 25, underline "1730"

Column 7, line 46, change ---(1.3-dithian2-yl)--- to "(1.3-dithian-2-yl)"

Column 8, lines 11 and 12, delete "-2" before ---methyl--- and insert "-2-" after ---cyclopentene---

Colunn 8, line 68, change ---helt-2- --- to "hept-2-"

Column 9, line 36, underline "1710"

Column 12, line 58, change ---hept-2-2-en--- to "hept-2-en"

Signed and Sealed this

Twentieth Day of July 1976

[SEAL]

Attest:

RUTH C. MASON
*Attesting Officer*

C. MARSHALL DANN
*Commissioner of Patents and Trademarks*